US005099835A

United States Patent [19]

Nelepka

[11] Patent Number: 5,099,835

[45] Date of Patent: * Mar. 31, 1992

[54] LIGHTWEIGHT BREATHING DEVICE

[76] Inventor: Guy S. Nelepka, 2327 N. Tustin Ave., Newport Beach, Calif. 92660

[*] Notice: The portion of the term of this patent subsequent to May 29, 2007 has been disclaimed.

[21] Appl. No.: 528,248

[22] Filed: May 24, 1990

Related U.S. Application Data

[63] Continuation-in-part of Ser. No. 293,071, Jan. 3, 1989, Pat. No. 4,928,686.

[51] Int. Cl.[5] .......... A61M 16/00

[52] U.S. Cl. .......... 128/204.18; 128/204.26; 128/205.24

[58] Field of Search .......... 128/205.22, 205.24, 128/204.26, 204.18

[56] References Cited

U.S. PATENT DOCUMENTS

| | | | |
|---|---|---|---|
| 4,297,998 | 11/1981 | Christianson | 128/204.26 |
| 4,798,203 | 1/1989 | Bartos | 128/205.22 |
| 4,928,686 | 5/1990 | Nelepka | 128/205.24 |

*Primary Examiner*—Edgar S. Burr
*Assistant Examiner*—Aaron J. Lewis
*Attorney, Agent, or Firm*—Willie Krawitz

[57] ABSTRACT

A lightweight breathing device for underwater use, and in contaminated air is disclosed. The device employs a one-way valve which requires only one hand to effect operation, and a closure stem which is securely mounted against excessive air pressure from the valve when air is released therethrough from an attached air tank. The one-way valve includes two interfitting components, one of which is rotatable, and which provides air orifices that form an air connection upon rotation to permit the release of air from the air tank.

8 Claims, 2 Drawing Sheets

LIGHTWEIGHT BREATHING DEVICE

This application is a continuation-in-part of U.S. Ser. No. 293,071; filed Jan. 3, 1989, and now U.S. Pat. No. 4,928,686 issued May 29, 1990.

BACKGROUND OF THE INVENTION

This invention relates to a new and improved portable breathing device which may be employed for underwater purposes, and for use above water in contaminated air situations, and where emergency alternative air supply sources are required.

Typically, the portable breathing device of this invention is used in conjunction with a lightweight air supply for relatively short periods of time, say 2-5 minutes, or longer, depending on the capacity of the air supply tank. The device of this invention is lightweight, and of a sturdy construction, which enables it to be easily manipulated. The lightweight feature of this device permits the user a greater degree of mobility in escaping to a safe location without being encumbered by heavy air tanks or cumbersome or awkward air supply lines.

Some prior art breathing devices have used poppet valve components which pose a hazard to the user in that they can be ejected form the device with considerable force an injure the user, or persons nearby.

Other prior art devices use a burst disc which may pose a hazard to the user due to inadequate design.

THE INVENTION

According to the invention, there is provided a breathing device with a unique on-off air release mechanism to an air supply tank which may be operated with one hand, and a simple and safe air release closure mechanism which enable the user to release air at controlled intervals for breathing purposes.

The on-off air release mechanism includes interfitting components, one of which is rotatable, and each of these components provides air connecting orifices which permit air to be released form the air supply tank to the air release closure mechanism. Both the on-off air release mechanism and the air release closure can be operated with the same hand.

DESCRIPTION OF THE PREFERRED EMBODIMENTS

Figure 1A:
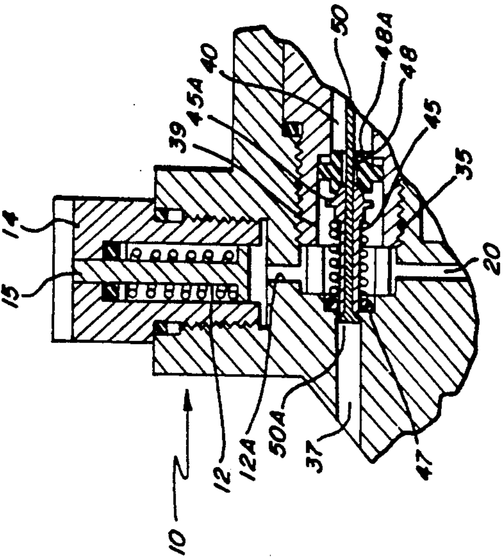
FIG. 1A is an enlarged view of a portion of FIG. 1.
Figure 1:
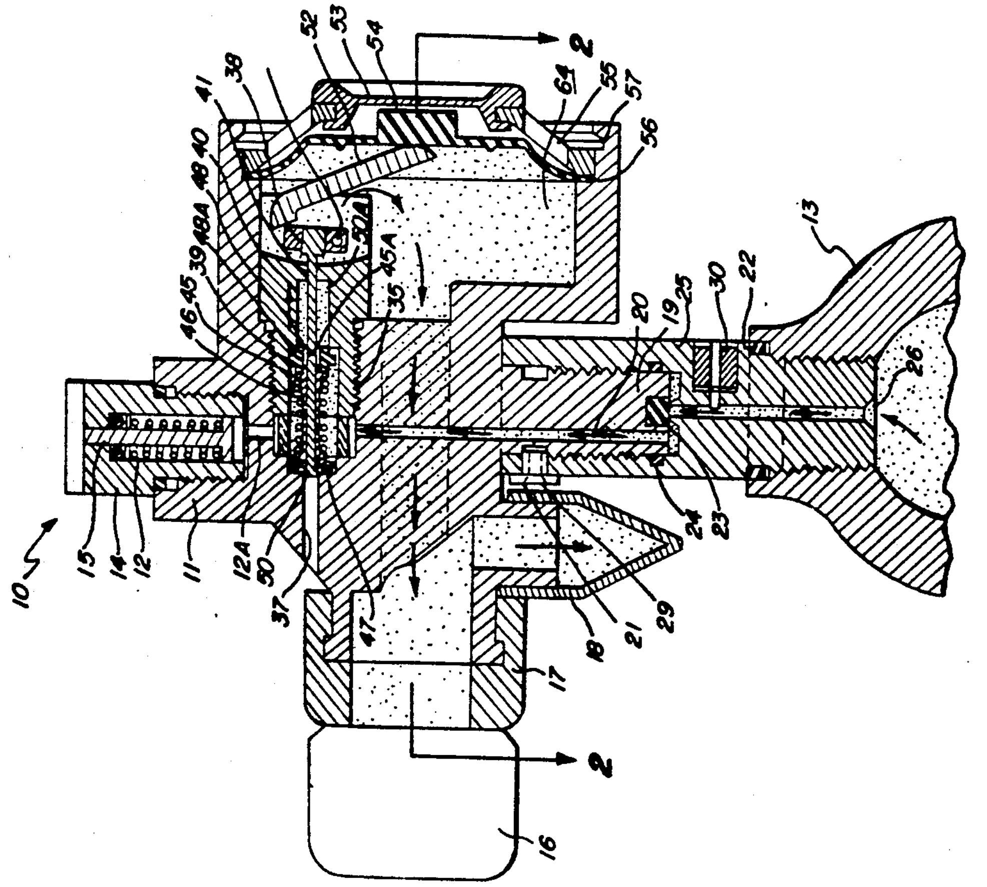
FIG. 1 is a cross sectional view in side elevation of the device of this invention.

The breathing device 10 of this invention is shown in FIG. 1, and comprises a body portion 11, fill port 12, and an air tank 13 which is filled with air through the fill port 12 and bore 12*a*, using a refill adaptor attached to a refill supply tank (not shown). After the air tank 13 has been filled, the breathing device 10 is shut off, and the adaptor and supply tank are removed, and a seal plug 14 bearing a spring loaded pressure gauge stem 15 are mounted in the port 12 to seal the device. When the air tank is loaded, it weighs about 2-5 pounds, with a reserve capacity of about 2-5 minutes based on continuous or intermediate breathing.

A breathing mouthpiece 16 is attached to the forward end of the device 10 through a connector 17, and an exhaust element 18 is employed to pass exhaust air from the user. An on-off housing insert valve 19 is formed as an integral part of the body portion 11 and defines an on-off center, longitudinal bore 20, and a 270 degree stop screw bore 21. The on-off housing insert valve 19, valve seat 23, and a valve 0-ring 24 fit into a rotatable steel cylinder stem 25, the latter defining a burst disc port 22. A longitudinal bore 26 is defined by the cylinder stem 25 to form an air connection with bore 20 when the cylinder stem 25 rotates through a 270 degree turn. When the valve 19 turns on, it admits air from the air tank 13 into the breathing device. The rotatable cylinder stem 25 may be conveniently operated with one hand only, thereby enabling the air supply from the air tank to be easily turned on or off.

A stop screw 29 is threaded into the stop screw bore 21 to prevent turning cylinder stem 25 past the air connection region of the longitudinal bores 20 and 26. Hence, it is not necessary for the user to make any special effort or any adjustment procedures to effect opening or close the on-off valve, since the air connection between bores 20 and 26 will occur as the stop screw 29 is rotated between 70 degrees and the full 270 degrees, A burst disc 30 is fitted into the burst disc port 22 of the cylinder stem 25 to guard against over pressurization of the breathing device, and is positioned to reduce internal or external damage to the breathing device if over pressurization occurs. Thus, if the user is holding the body portion 11 of the device, the burst disc 30 is positioned away from the user. Hence, rupture of the burst disc will occur away from the user, and will not be directed into the device.

An air regulator housing 38 is threadably mounted within a bore 35, and is air connected to the bores 20 and 26 of the housing insert valve 19 and the cylinder stem 25 through a body portion 36 positioned along lines 2—2 of FIG. 1. The body portion 36 is shown in greater detail in FIG. 2, and will be described, infra. Air pressure is balanced to ambient through an atmospheric air bore 37 which is connected to a poppet bore cavity 19 of an air regulator housing 38.

The regulator housing 38 is threadably mounted in the body portion 11, and defines the poppet bore cavity 39, a poppet stem cavity 40, and a poppet stem bore 41. A poppet 45, having a head end 45*a* is secured within the poppet bore cavity 39 of the regulator housing 38 by a spring 46 and sealed at the entrance to the air pressure equalization bore 37 by an O-ring 47. The head end 45*a* of the poppet seats and seals off a regulator housing seat 48 in conjunction with an O-ring 48*a*.

A poppet stem 50 providing an integrally formed shoulder is mounted or molded within the poppet 45 and is firmly attached thereto by means of a roughened exterior surface. Alternatively, the poppet stem 50 may employ only a roughened surface and attach within the poppet 45 without a shoulder construction. Another possible construction may employ the formed shoulder 50*a* mounted into a cavity bore in head end 45*a*. The poppet stem 50 passes through the poppet stem cavity 40 and poppet stem bore 41, and is secured by pivot lever 51. A purge lever 52 is employed to actuate the pivot lever 51 and drive the poppet stem 50 and the poppet 45 from the regulator housing seat 48, to allow air flow and purging. An adjustment screw (not shown) is adapted to preset the tension of the spring 46 so that water pressure at atmospheric applied through the air equalization bore 37 will be sufficient to maintain the poppet closed.

The construction of the poppet stem 50 with a roughened surface and/or shoulder 50a provides a safe arrangement since it is unlikely that the poppet stem will dislodge from the poppet 45 and be driven out of the device. This will prevent injury to a user or persons nearby.

Figure 2:
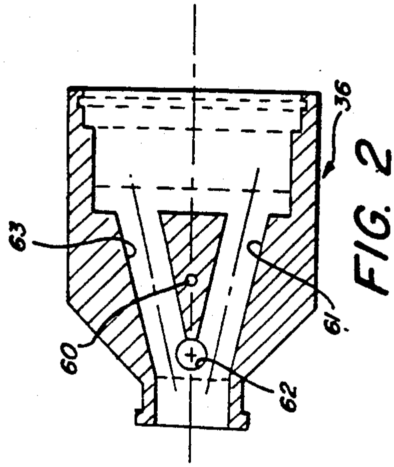
FIG. 2 is a plan view of the device, taken along lines 2—2 of FIG. 1.

Finger or suction pressure applied to the purge lever 52 will be applied to the poppet stem 50 by means of an assembly comprising a purge button 53 acting upon a diaphragm 54, the latter being reinforced by a diaphragm disc 58. The purge button 53 is surrounded by a cover 55, and the assembly is secured within a circular shoulder 56 along with a diaphragm retainer 57. When the purge button 53 is pressed, water and moisture will be expelled from the device through an exhaust bore 62 of body portion 36, and out exhaust element 18, as shown in FIGS. 1 and 2. A bore 60 of body portion 36 connects with the longitudinal bore 20 of the on-off housing insert valve 19, and admits air from the air tank 13 to the device when the cylinder stem 25 is rotated to air connect bore 26 with bore 20. When the purge button is pressed, the poppet 45 is unseated from the regulator housing seat 48. This releases or blows out water and moisture along manifolds 61 and 63 of body portion 36, through exhaust port bore 62, and to the exhaust element 18, as shown in FIGS. 1 and 2.

When the user draws on the mouthpiece 16, sufficient suction causes the poppet 45 to unseat and admit air to an inner chamber 64 along manifold channels 61 and 63 of the body 36 to the mouthpiece, and hence the user. When the user exhales, the poppet will close and exhaust air will pass through the bore 62 and out exhaust element 18.

The breathing device of FIGS. 1, 1A and 2 is adequate for pressures of about 1,800 psi. However, for higher pressures of about 3,000 psi, it would be preferred to modify the device to reduce the possibility of component blow-out, and to reduce the effects of the high pressures on the stem-poppet, cylinder springs, and gasket components. Also, it would be desirable to reduce the air pressure supplied to the user, because if the air pressure is too high, it tends to be wasted by the user.

Figure 5:
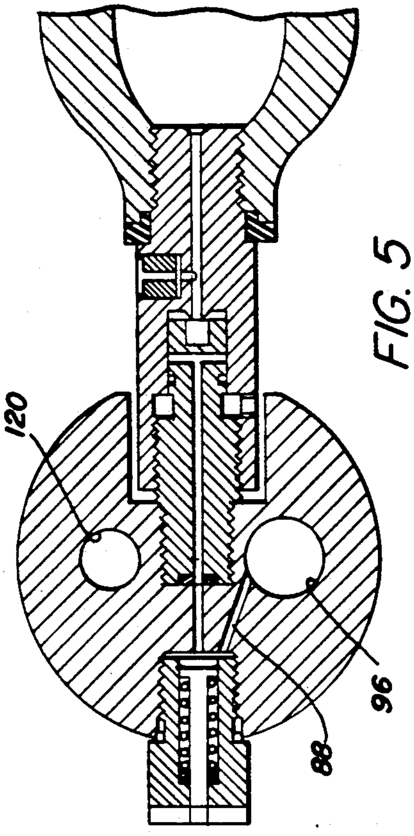
Figure 4:
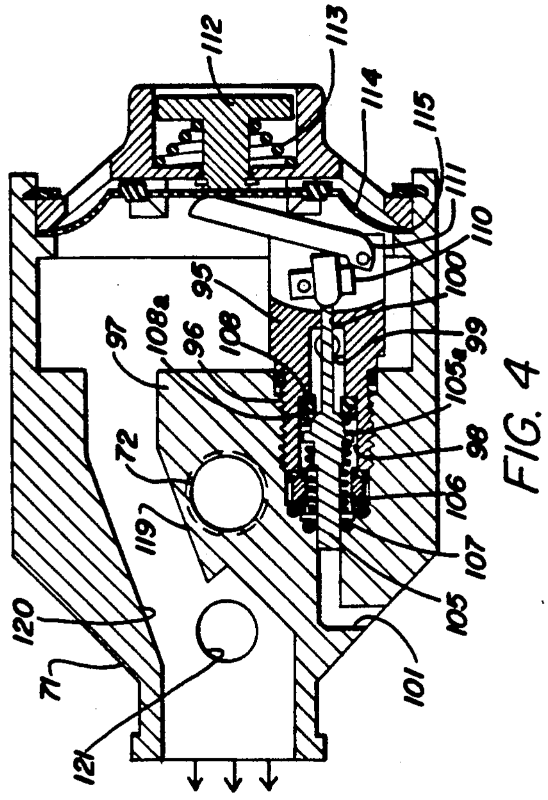
FIG. 4 is a cross sectional view in plan of the poppet valve and actuating mechanism of FIG.3; and, FIG. 5 is a sectional view in rear elevation showing the interconnecting air ports, and air flow from an external air supply and from an attached air supply tank of FIG. 3.
Figure 3:
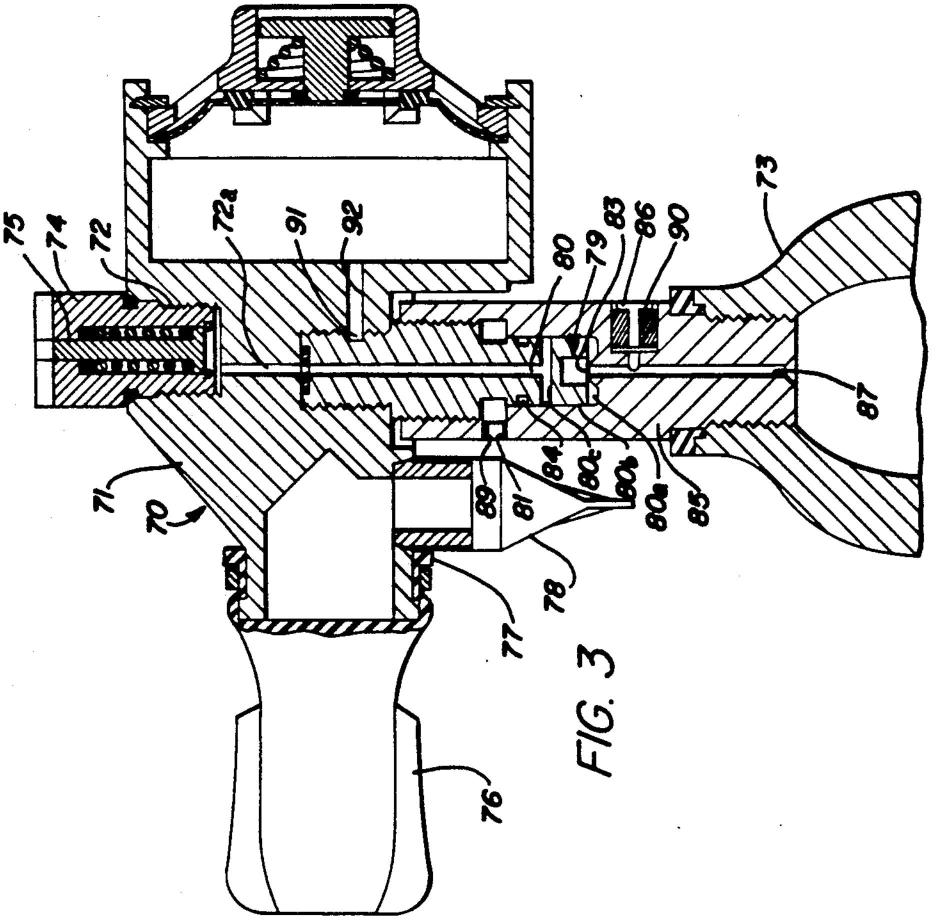
FIG. 3 is a cross sectional view in side elevation of another embodiment the device of this invention.

The modified breathing device 70 is shown in FIGS. 3, 4 and 5, and comprises a body portion 71, fill port 72, and air tank 73 which is filled with air through the fill port and bore 72a, using a refill adaptor attached to a refill supply tank (not shown). After the air tank 73 has been filled, the breathing device 70 is shut off and the adaptor and supply tank are removed. A seal plug 74 bearing a spring loaded pressure gauge stem 75 are then mounted in the fill port 72 to seal the device. When the tank is loaded, it weighs about 5–10 pounds, with a reserve capacity of about 7–10 minutes based on continuous or intermediate breathing.

A breathing mouthpiece 76 is attached to the forward end of the breathing device 70 through a connector 77, and an exhaust element 78 is employed to pass exhaust air from the user. An on-off housing insert valve 79 is formed as an integral part of body portion 71 and defines a longitudinal bore 80, and a 270 degree stop screw bore 81. A chamber 80a is formed at the bottom of the insert valve 79 and between a cylinder stem 85. The chamber 80a connects with a peripheral space 80b which is formed between valve 79 and the stem 85. The bottom of bore 80 terminates in a space 80c which connects with the peripheral space 80b.

The on-off housing insert valve 79, a valve seat 83 and a valve 0-ring 84 all fit into the rotatable steel cylinder stem 85, the latter defining a burst disc port 86. A longitudinal bore 87 is defined by the cylinder stem 85 to form an air connection with bore 80 when the cylinder stem 85 rotates through a 270 degree turn. When the housing insert valve 79 is turned on, it unseats from the valve seat 83 and air is admitted from the air tank 73 into the breathing device through connecting bore 87, chamber 80a, peripheral space 80b, space 80c and bores 80, 72a and 88, and then into a regulator housing bore 96, described, infra. The rotatable cylinder stem 85 may be conveniently operated, thereby enabling the air supply from the air tank 73 to be easily turned on or off.

When filling the air tank 73 to operating pressures, air flows linearly and directly from air port 72 and bores 72a, 80 and 87, while effectively by-passing the poppet-stem, spring mechanism and seals. Hence, wear and tear on these components is reduced despite the increase in air pressure from about 1800 psi used in the embodiments of FIGS. 1, 1A and 2, to about 3000 psi for that shown in FIGS. 3, 4 and 5.

A stop screw 89 is threaded into the stop screw bore 81 to prevent turning cylinder stem 85 past the air connection region of the longitudinal bores 80 and 87. Hence, it is not necessary for the user to make a special effort or adjustment to effect opening or closing of the on-off valve, since air connection between bores 80 and 87 will occur as the stop screw 89 is rotated between the 70–270 degree range.

A burst disc 90 is fitted into the burst disc port 86 of the cylinder 85 to guard against over pressurization of the breathing device, and is positioned to prevent any internal or external damage to the breathing device if over pressurization occurs. Thus, if the user is holding the body portion 71 of the device, the burst disc 90 is positioned away from the user. Hence, rupture of the burst disc will occur away from the user, and will not be directed into the device. A set screw 91 positioned within a bore 92 functions to prevent the insert valve from rotating due to the high pressures employed.

As shown in FIG. 4, an air regulator housing 95 is threadably mounted within a housing bore 96 in the body portion 71. The housing 95 is air connected to the bores 80 and 87 of the housing insert valve 79 and cylinder stem 85 through bores 88 and 72a passing through a body portion 97. The regulator housing 95 defines a poppet bore cavity 98, a poppet stem cavity 99, and poppet stem bore 100. Air pressure is balanced to ambient through an air equalization bore !01 which is connected to the poppet bore cavity 98 of the air regulator housing 95.

A poppet 105, having a head end 105a, is secured and biased by a spring 106 within the poppet bore cavity 98 of the air regulator housing 95. The poppet is sealed at the entrance to the air pressure equalization bore 101 using an O-ring 107. The head end 105a of the poppet seats and seals off a regulator housing seat 108, in conjunction with an O-ring 108a. A poppet stem 109 is shown integrally formed with the poppet 105. Alternatively, the poppet stem can be secured or molded into the poppet in a similar manner as shown in the embodiments of FIGS. 1, 1A, and 2. The poppet stem 109 passes through the poppet stem cavity 99 and poppet stem bore 100, and is driven by pivot lever 110. A purge lever 111 actuates the pivot lever 110, and the purge lever is driven by a purge button 112 biased by a spring 113 which is secured by a diaphragm 114 mounted within a circumferential shoulder 115.

As shown in FIG. 4, a manifold area 119 is mounted within the body portion 91 and defines single channel 120 which connects from the air regulator housing to the breathing mouthpiece 76, as shown by the arrows; exhaust air is fed through bore 121. Use of the single channel 120, rather than the double channel 61 and 63 as shown in FIG. 2, enables better control of the air intake by the user. This control by the user is particularly important when the device is employed at a relatively higher pressure of 3000 psi, and reduces the tendency of a user to waste air. Operation of the purge button 112 and the device 70 is the same as described for the embodiments of FIGS. 1, 1A and 2.

The device of this invention is simple to operate, and the components of the breathing device do not present a problem of exploding parts. Use of the present device, when underwater, can become critically important as a back-up device if a major air system fails, because it is portable and totally independent of the major air supply system, and it enables the user adequate time and leeway to escape due to failure of a life support system. It will also be appreciated that in a smoke or contaminated air environment, the lightweight nature and ease of operation enables a user to avoid reliance on a much heavier air supply system. The same situation would prevail if there were no available air supply system or if a permanently attached air supply system were to malfunction or fail.

I claim:

1. An air breathing device, comprising:

a. a main body including a fill port for supplying air to an air supply tank mounted on the breathing device;

b. a rotatable cylinder stem defining a first orifice bore, the cylinder stem being mounted on the breathing device and attached to the air supply tank, the first orifice bore being connected to the air supply tank;

c. an on-off valve mounted on the cylinder stem and defining a second orifice bore, the first and second orifice bores being adapted to form an air connection upon sufficient rotation of the cylinder stem, thereby turning on and admitting air from the air supply tank to the device;

d. an air regulator housing mounted within the main body and connecting from the second orifice bore to a poppet bore cavity, the main body defining an air bore connection leading linearly from the fill port to the air supply tank, the air regular housing being off-line from the linear flow between the fill port and the air supply tank;

e. an elongate, spring loaded poppet means defining a longitudinal, axial bore, one end of the poppet means seating into an atmospheric bore, and an opposed end of the poppet means, including a poppet head, seating into and sealing the poppet bore cavity, and a poppet stem mounted and secured within the longitudinal, axial bore the poppet;

f. a body portion mounted in the on-off valve and providing an air connection between the valve and the poppet means of the air regulator housing;

g. a breathing mouthpiece and exhaust port mounted on the air breathing device, the breathing mouthpiece being air connected through the body portion to the air regulator, housing and the poppet bore cavity, the exhaust port being connected to the body portion; and, h. a lever adapted to actuate the stem of the poppet means, the poppet stem being connected to the lever through a poppet stem cavity contiguous with the poppet bore cavity and secured in the poppet stem cavity by a shoulder on the poppet stem; whereby:

i. when the on-off valve is turned on, and a user inhales on the mouthpiece, sufficient suction is produced to unseat the poppet from the poppet bore cavity and admit air to the user from the air supply tank and through the connected first orifice bore, and then through the body portion;

ii. when the user exhales on the mouthpiece, the poppet closes and exhaust air passes through the body portion to the exhaust port; and, iii. when the lever is pressed, the poppet will be unseated and release or blow out water and moisture through the body portion and exhaust port.

2. The air breathing device of claim 1, including an air cylinder attached to the cylinder stem for supplying air therethrough.

3. The air breathing device of claim 1, including a burst disc positioned away from the said mouthpiece.

4. The air breathing device of claim 1, including stop screw means to enable air connection between the first and second bores of the cylinder stem and on-off valve, respectively, to be made over a wide area of rotation of the cylinder stem.

5. The air breathing device of claim 1, in which the poppet stem, at an end remote from the poppet head, is positioned for movement within an atmospheric air bore, and water or air at atmospheric pressure will maintain the poppet closed.

6. The air breathing device of claim 1, in which the poppet stem provides a roughened surface to firmly attached the poppet stem to the poppet.

7. The air breathing device of claim 1, adapted for pressurization from about 1,800 psi to about 3,000 psi.

8. The air breathing device of claim 1, in which the breathing mouthpiece is air connected to the air regulator housing by a single channel manifold.

* * * * *